United States Patent [19]

Kajander

[11] Patent Number: 4,822,332
[45] Date of Patent: Apr. 18, 1989

[54] DEVICE FOR DELIVERING AN OBJECT TO A CAVITY

[75] Inventor: Richard E. Kajander, Ware, Mass.

[73] Assignee: Tambrands Inc., Lake Success, N.Y.

[21] Appl. No.: 176,371

[22] Filed: Mar. 31, 1988

[51] Int. Cl.$^4$ ............................................. A61F 13/20
[52] U.S. Cl. ......................................... 604/16; 604/904
[58] Field of Search ....................... 604/11–18, 604/904, 59–61

[56] References Cited

U.S. PATENT DOCUMENTS

| D. 191,481 | 10/1961 | Conley | D74/1 |
|---|---|---|---|
| D. 235,686 | 7/1975 | Schoenfeld et al. | D83/1 Q |
| D. 240,462 | 7/1976 | Dash | D83/12 A |
| D. 240,464 | 7/1976 | Dash | D83/12 A |
| D. 250,663 | 12/1978 | Koch et al. | D24/99 |
| 921,130 | 5/1909 | Lockwood | |
| 2,094,268 | 9/1937 | Friedman | 138/78 |
| 2,105,710 | 1/1938 | Wadel | 128/264 |
| 2,546,754 | 3/1951 | Jones | 128/260 |
| 3,025,004 | 3/1962 | Levi | 239/33 |
| 3,084,693 | 4/1963 | Cathcart | 128/349 |
| 3,124,134 | 3/1964 | Gardner | 128/263 |
| 3,154,080 | 10/1964 | Rowan et al. | 128/349 |
| 3,326,695 | 6/1967 | Neuhauser | 99/138 |
| 3,340,869 | 9/1967 | Bane | 128/2 |
| 3,346,187 | 10/1967 | Mueller | 239/33 |
| 3,358,686 | 12/1967 | Asaka | 128/263 |
| 3,409,224 | 11/1968 | Harp et al. | 239/33 |
| 3,433,391 | 3/1969 | Krizka et al. | 222/95 |
| 3,438,578 | 4/1969 | Peterson et al. | 239/33 |
| 3,473,524 | 10/1969 | Drewe | 128/2 |
| 3,543,754 | 12/1970 | Jones, Sr. | 128/263 |
| 3,570,662 | 3/1972 | Polyak | 206/63.2 |
| 3,572,393 | 3/1972 | Eisert | 138/121 |
| 3,581,944 | 6/1971 | Jeppesen | 222/107 |
| 3,595,233 | 7/1971 | Fuchslocher et al. | 128/264 |
| 3,597,517 | 8/1971 | Smith | 264/97 |
| 3,606,889 | 9/1971 | Arblaster | 128/349 |
| 3,674,025 | 7/1972 | Bleuer | 128/263 |
| 3,714,311 | 1/1973 | Stefanka | 264/98 |
| 3,721,371 | 3/1973 | Dolveck | 222/386.5 |
| 3,749,093 | 7/1973 | Bloom | 128/263 |
| 3,759,258 | 9/1973 | Loyer | 128/263 |
| 3,805,786 | 4/1974 | Bernardin et al. | 128/263 |
| 3,807,399 | 4/1974 | Morman et al. | 128/263 |
| 3,826,409 | 7/1974 | Chilcoate | 222/107 |
| 3,835,856 | 9/1974 | Warncke | 128/263 |
| 3,844,284 | 10/1974 | Schoenfeld et al. | 128/232 |
| 3,872,994 | 3/1975 | Hyde | 220/1 R |
| 3,908,704 | 9/1975 | Clement et al. | 138/21 |
| 3,952,341 | 4/1976 | Cain | 4/255 |

(List continued on next page.)

FOREIGN PATENT DOCUMENTS

| 3540725 | 5/1986 | Fed. Rep. of Germany . |
|---|---|---|
| 574258 | 4/1980 | Japan . |
| 574259 | 5/1980 | Japan . |
| 2033754 | 5/1980 | United Kingdom . |
| 2081586 | 2/1982 | United Kingdom . |

Primary Examiner—John D. Yasko
Assistant Examiner—Mark O. Polutta
Attorney, Agent, or Firm—John E. Nathan; Jeffrey H. Ingerman

[57] ABSTRACT

An applicator for delivering an object, such as a menstrual tampon, to a cavity, such as the vaginal canal, which applicator is not much longer than the object when delivered to the user, is provided. The applicator is a unitary injection blow-molded device which includes a first tubular section housing the object, a second collapsible and extensible corrugated tubular section abutting the first section, and a third tubular section abutting the second section and serving primarily as a handle. An integral pusher member is formed in the interior of the applicator attached to the inner wall of the third section, and is biased to assume a position along the centerline of the applicator. The applicator is delivered to the user in a collapsed state, with the pusher alongside the object in the first section. The user extends the object by pulling on the first and third sections, withdrawing the pusher from the first section so that it aligns itself behind the center of the object. The applicator is inserted in the cavity and the object is ejected by pushing the third section toward the firsts section, collapsing the second section and driving the pusher member forward.

18 Claims, 4 Drawing Sheets

U.S. PATENT DOCUMENTS

| | | | |
|---|---|---|---|
| 4,044,836 | 8/1977 | Martin et al. | 169/30 |
| 4,079,757 | 3/1978 | Fischer et al. | 138/121 |
| 4,148,317 | 4/1979 | Loyer | 128/263 |
| 4,187,960 | 2/1980 | Bonk | 222/107 |
| 4,211,225 | 7/1980 | Sibalis | 128/285 |
| 4,216,801 | 8/1980 | Aykanian | 138/121 |
| 4,273,125 | 6/1981 | Sakurai | 128/263 |
| 4,276,881 | 7/1981 | Lilaonitkul | 128/263 |
| 4,286,594 | 9/1981 | Cunningham | 128/263 |
| 4,286,595 | 9/1981 | Ring | 128/263 |
| 4,291,696 | 9/1981 | Ring | 128/263 |
| 4,312,348 | 1/1982 | Friese | 128/263 |
| 4,318,404 | 3/1982 | Cunningham | 128/263 |
| 4,351,339 | 9/1982 | Sneider | 128/285 |
| 4,413,986 | 11/1983 | Jacobs | 604/14 |
| 4,479,791 | 10/1984 | Sprague | 604/14 |
| 4,496,341 | 1/1985 | Brucks | 604/14 |
| 4,515,842 | 5/1985 | Kovacs | 428/36 |
| 4,526,296 | 7/1985 | Berger et al. | 222/107 |
| 4,543,086 | 9/1985 | Johnson | 604/11 |
| 4,648,867 | 3/1987 | Conner et al. | 604/14 |
| 4,699,610 | 10/1987 | Hanano et al. | 604/16 |

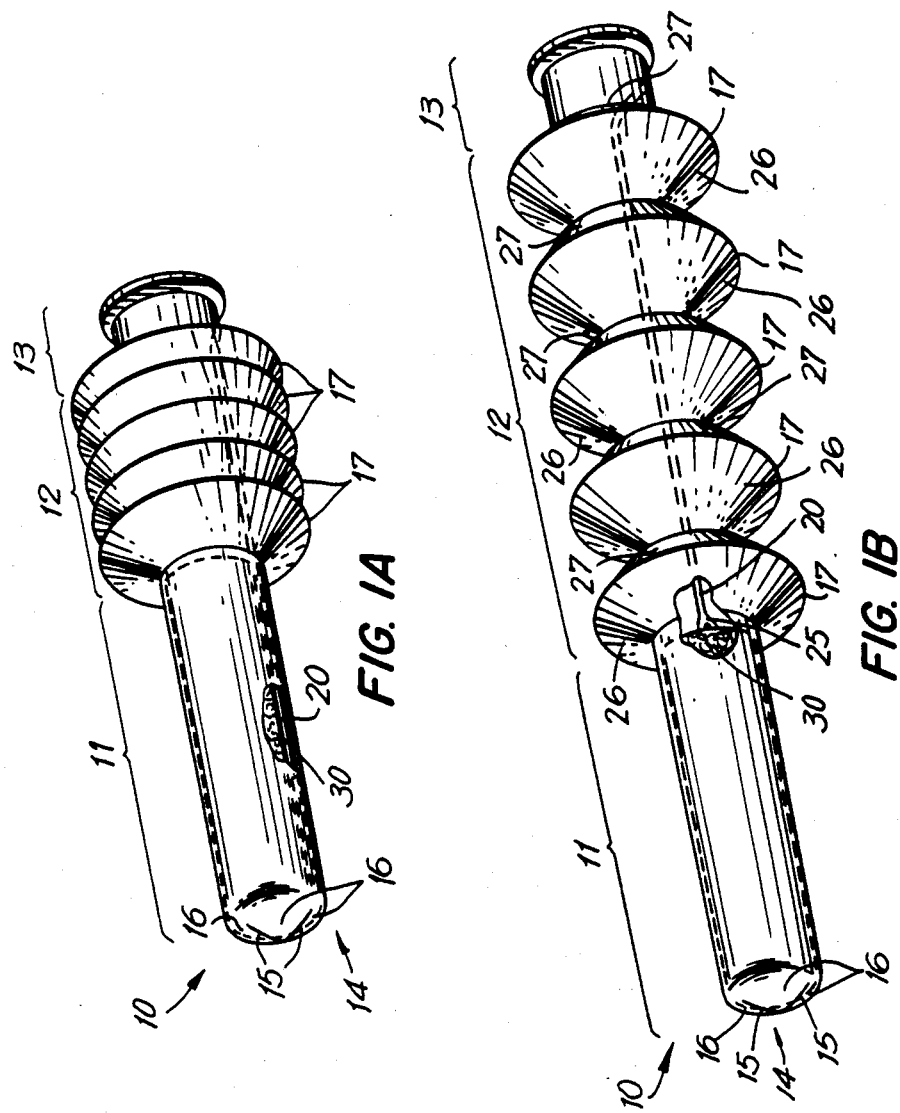

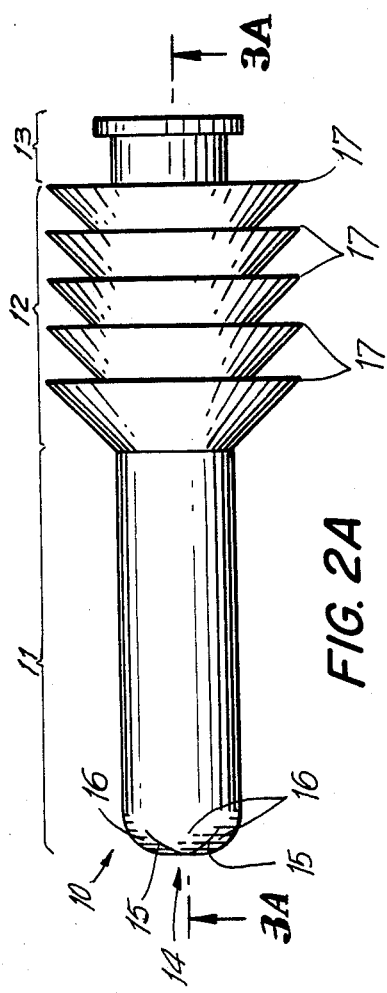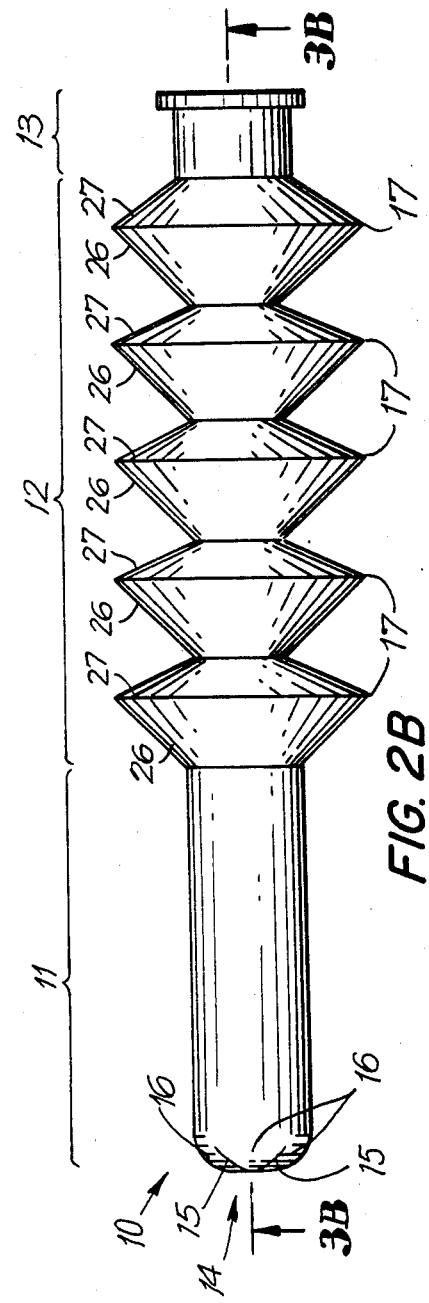

DEVICE FOR DELIVERING AN OBJECT TO A CAVITY

BACKGROUND OF THE INVENTION

This invention relates to a unitary device for storing an object and delivering the object to a cavity. More particularly, this invention relates to a tampon applicator for inserting a menstrual tampon into the vaginal canal.

Menstrual tampons have frequently been inserted into the vaginal canal using a two-part applicator, typically made of paper, cardboard or plastic. Many applicators include two telescoping tube sections, both of which are longer than the tampon. The tampon rests toward one end (the "front" or "exit" end) of the section of larger diameter, and the section of smaller diameter is inserted into the other end of the section of larger diameter. The overall assembly is thus approximately twice the length of a tampon. When the tampon is to be inserted into the vaginal canal, the front end is inserted into the vagina, the two tube sections are grasped, and the smaller diameter section is moved inward while the larger diameter section is held in place, so that the smaller diameter section bears against the tampon and pushes it from the applicator into the vaginal canal.

Tampons with applicators as described above are of necessity packaged with the applicators in the extended state in which each is twice the length of a tampon alone. Therefore, the packaging of such tampons must have a dimension twice the length of a tampon.

More recently, tampon applicators have been devised in which the smaller diameter tube section comes pushed into the larger diameter tube section, between the tampon and the inner wall of the larger diameter tube section. Thus, the packaged assembly is only slightly longer than the tampon itself. To insert the tampon, the user grasps the larger diameter tube section and a projecting portion of the smaller diameter tube section and pulls the smaller diameter tube section out of the larger diameter tube section, leaving the tampon in the larger diameter tube section. In some embodiments, a hook is provided on the inner surface of the larger diameter tube section to retain the tampon in place while the smaller diameter tube section is being withdrawn. Once the smaller diameter tube section has been withdrawn, the applicator functions like that described above.

Tampon applicators of this type are generally formed of pastic, which can be molded to provide the retaining hook, as well as stops that prevent the smaller diameter tube section from being completely withdrawn from the larger diameter tube section. The protruding portion of the smaller diameter tube section can also be molded with a textured surface or some form of grip to facilitate its withdrawal from the larger diameter tube section. However, even applicators of this type must be fabricated in two pieces.

It would be desirable to be able to provide a tampon applicator which when packaged is not much longer than a tampon itself, and which is formed in one piece.

SUMMARY OF THE INVENTION

It is an object of this invention to provide a tampon applicator which when packaged is not much longer than a tampon itself, and which is formed in one piece.

In accordance with this invention, there is provided a unitary device, such as a tampon applicator, for delivering an object, such as a menstrual tampon, to a cavity, such as the vaginal canal. The device comprises a substantially rigid first tubular section for containing the object to be inserted. The tubular section has an exit end through which the object is inserted into the cavity. A second tubular section abuts the first tubular section and is collapsible and extensible. A substantially rigid third tubular section abuts the collapsible and extensible second section. A pusher member is mounted at a first end thereof to an inner wall of the device at an end remote from the exit end and extends through the second section into the first section, a second end of the pusher member being biased away from the inner wall. The pusher member has a length such that when the second section is collapsed, the second end reaches at least to the exit end, and when the second section is extended, the second end reaches at most to a point at which the first and second tubular sections abut one another. When the object is in the device prior to insertion into the cavity, the second section is collapsed and the pusher member lies in a first position relative to the inner wall, between the inner wall and the object, in the first section. When the object is to be inserted, the second section is extended by grasping the first section and the remote end and moving them away from one another, whereby the pusher member is withdrawn from between the inner wall and the object and, as a result of the bias, the second end thereof assumes a second position further from the inner wall than the first position and adjacent the object, thereby arming the device. When the exit end of the armed device is inserted in the cavity and the second section is collapsed by grasping the first section and the remote end and moving them toward one another, the pusher member pushes the object out of the exit end into the cavity.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which:

FIG. 1A is a fragmentary perspective view taken from the exit end of a tampon applicator according to this invention in its unarmed state;

FIG. 1B is a fragmentary perspective view taken from the exit end of a tampon applicator according to this invention in its armed state;

FIG. 2A is a side elevational view of the unarmed tampon applicator of FIG. 1A;

FIG. 2B is a side elevational view of the armed tampon applicator of FIG. 1B;

DETAILED DESCRIPTION OF THE INVENTION

Figure 3A:
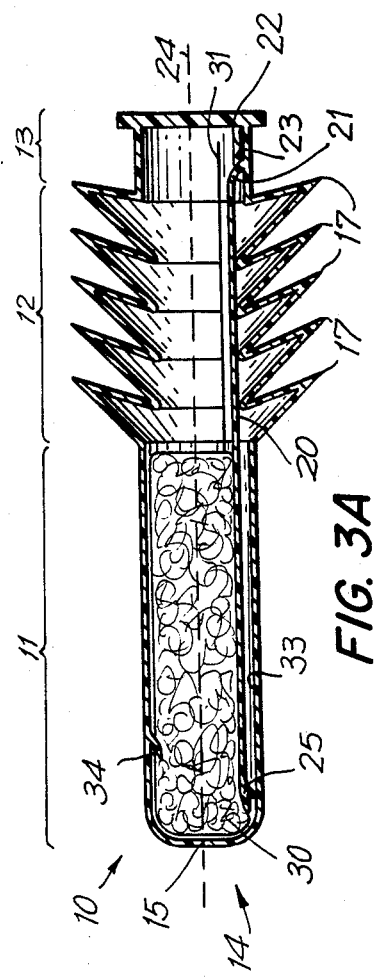
FIG. 3A is a longitudinal cross-sectional view of the unarmed tampon applicator of FIG. 2A, taken from line 3A—3A of FIG. 2A.

A tampon applicator according to the present invention is shown in FIGS. 1A-4. Applicator 10 has first, second and third tubular sections 11, 12, 13. Second tubular section 12 is alternately collapsible and extensible, while first and third tubular sections 11, 13 are substantially rigid, at least as compared to section 12. First section 11 abuts second section 12 at one end of section 12, while third section 13 abuts second section 12 at the other end of section 12. A pusher member 20 is provided within applicator 10. A first end 21 of pusher member 20 is mounted to the inner wall 22 of third section 13 at 23, in such a way (described below) that it is biased to assume a position, if not restrained, along centerline 24 of applicator 10.

Applicator 10 is provided with tampon 30 in first tubular section 11. Tampon 30 is of any suitable construction, and preferably includes withdrawal cord 31 in a known manner.

FIGS. 1A, 2A and 3A show applicator 10 as it is delivered to the user. Tampon 30 is in first tubular section 11. Second tubular section 12 is collapsed. Pusher member 20 is captured between inner wall 33 of first section 11 and tampon 30.

Figure 3B:
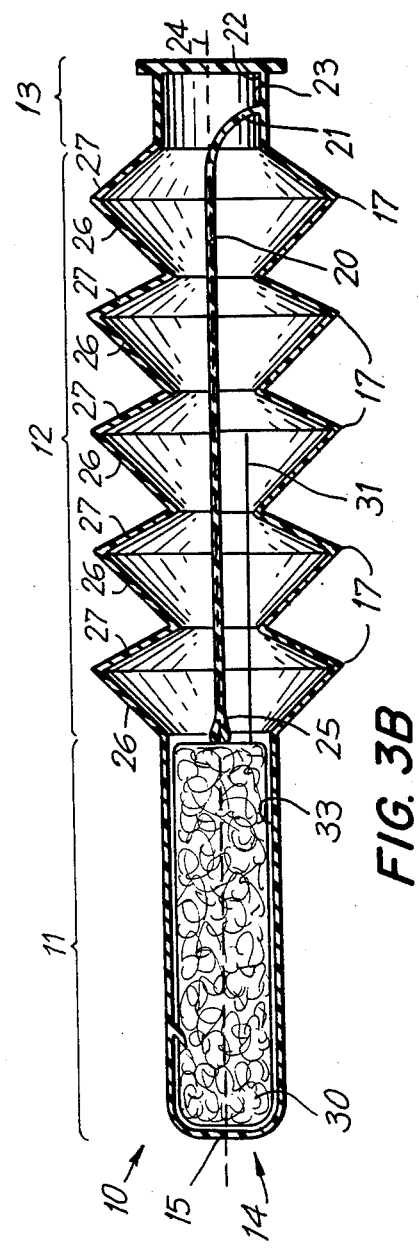
FIG. 3B is a longitudinal cross-sectional view of the armed tampon applicator of FIG. 2B, taken from line 3B—3B of FIG. 2B.

In order to insert tampon 30 into the vaginal canal, the user must first "arm" applicator 10 by grasping first and third sections 11, 13 and pulling them away from one another, thereby extending second section 12. FIGS. 1B, 2B and 3B show applicator 10 in its armed state, after the user has extended second section 12. The extension of second section 12 causes pusher member 20 to be withdrawn from between tampon 30 and inner wall 33 of section 11. Once free, pusher member 20 assumes a position, under the influence of the bias referred to above, along centerline 24, with its second end 25 directly behind tampon 30. Friction between tampon 30 and inner wall 33 may be sufficient to prevent tampon 30 from being withdrawn from section 11 as pusher member 20 is withdrawn, but preferably hook 34 is provided to retain tampon 30 in section 11. Hook 34 is angled toward exit end 14 of applicator 10 so that it prevents tampon 30 from moving into second section 12, but does not interfere with the exit of tampon 30 through exit end 14.

Figure 4:
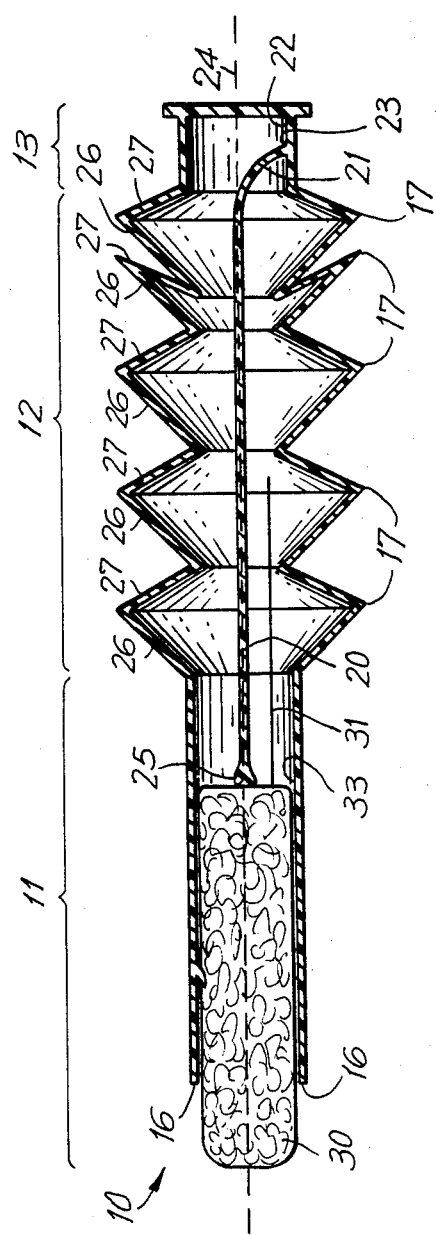
FIG. 4 is a longitudinal cross-sectional view of the tampon applicator of FIGS. 1A-3B in a partially discharged condition.

Once applicator 10 has been armed, the user inserts end 14 into the vaginal opening and grasps first and third sections 11, 13 and moves them toward one another, collapsing second section 12. Second end 25 of pusher member 20 bears against the rear end of tampon 30, forcing it out of end 14 of applicator 10 as seen in FIG. 4. End 14 is originally closed and rounded for easy and comfortable insertion into the vaginal opening, but is provided with slits 15 forming flaps 16 which are pushed aside as tampon 30 exits applicator 10.

In an alternative embodiment (not shown), third section 13 could be eliminated, with pusher 20 mounted at the end of second section 12 remote from exit end 14, the user grasping the remote end instead of third section 13.

Applicator 10 is preferably a unitary device formed, preferably, by injection blow molding from polyethylene. The ability of pusher member 20 to assume positions along the inner wall or along centerline 24, and the bias causing pusher member 20 to assume a position along centerline 24, are the result of the flexibility of the material from which it is formed and the unitary injection blow-molded formation of applicator 10.

Alternatively, applicator 10 can be formed by continuous blow molding or injection molding, and other materials, such as polyolefins other than polyethylene, or copolymers, might be used. In addition, applicator 10 might be assembled into a unitary device from two or more parts formed separately.

Collapsible and extensible second tubular section 12 is formed of a number of ribs or corrugations 17. Each corrugation 17 is preferably asymmetrical, having a long side 26 and a short side 27. This asymmetry allows the corrugations 17 to nest neatly in one another in the collapsed state, thereby minimizing the overall length of section 12 in the collapsed state, and also provides a toggle effect causing a detectable stop to the user as each corrugation 17 is extended or collapsed. Depending on the stiffness of the material from which applicator 10 is formed, an audible click may also be heard. The toggle effect also causes section 12 to maintain itself in any degree of extension or collapse selected by the user.

Other configurations may be used for section 12. For example, a collapsible thread or spiral may be used. Additional possible configurations include bellows or folding plates arranged to fold up on themselves.

The dimensions of applicator 10 and its various portions are determined primarily by the dimensions of tampon 30. The diameter is approximately the diameter of tampon 30. The length of first section 11 is approximately the length of tampon 30. The length of third section 13 is a short but comfortable length for grasping, as section 13 is primarily a handle which, as discussed above, may be omitted. The lengths of second section 12 and pusher member 20 are interrelated. Pusher member 20 cannot protrude from applicator end 14 when applicator 10 is in the unarmed state, but when tampon 30 is being ejected, pusher member 20 must reach all the way to end 14. Therefore, pusher member must reach end 14 while applicator 10 is in the unarmed state and section 12 is fully collapsed. The length of section 12 must be such that when it is fully extended, second end 25 of pusher member 20 reaches no further forward than the rear end of tampon 30, and preferably is immediately adjacent tampon 30. When applicator 10 is delivered loaded but unarmed to the user, its overall length is the combined lengths of first section 11, third section 13, and second section 12 in its collapsed state, and is not much longer than tampon 30 itself.

Applicator 10 could be used to deliver any other type of solid object to any suitable cavity, in addition to delivering menstrual tampons to the vaginal canal.

Thus it is seen that an applicator for delivering an object, such as a menstrual tampon, to a cavity, such as the vaginal canal, which applicator is not much longer than the object when delivered to the user, is provided. One skilled in the art will appreciate that the present invention can be practiced by other than the described embodiment, which is presented for purposes of illustration and not of limitation, and the present invention is limited only by the claims which follow.

What is claimed is:

1. A unitary device for delivering an object to a cavity, said device comprising:
   a substantially rigid first tubular section for containing said object to be inserted, said tubular section having an exit end through which said object is inserted into said cavity;
   a second tubular section abutting said first tubular section, said second section being collapsible and extensible; and
   a pusher member mounted at a first end thereof to an inner wall of said device at an end remote from said exit end and extending through said second section into said first section, a second end of said pusher member being biased away from said inner wall, said pusher member having a length such that when said second section is collapsed, said second end reaches at least to said exit end, and when said second section is extended, said second end reaches at most to a point at which said first and second tubular sections abut one another; wherein:

when said object is in said device prior to insertion into said cavity, said second section is collapsed and said pusher member lies in a first position relative to said inner wall, between said inner wall and said object, in said first section; and when said object is to be inserted, said second section is extended by grasping said first section and said remote end and moving them away from one another, whereby said pusher member is withdrawn from between said inner wall and said object and, as a result of said bias, said second end thereof assumes a second position further from said inner wall than said first position and adjacent said object, thereby arming said device; such that when said exit end of said armed device is inserted in said cavity and said second section is collapsed by grasping said first section and said remote end and moving them toward one another, said pusher member pushes said object out of said exit end into said cavity.

2. The device of claim 1 further comprising a substantially rigid third tubular section abutting said collapsible and extensible second section, said third section serving as a handle for grasping said remote end.

3. The device of claim 1 further comprising means for retaining said object in said first section while said pusher member is being withdrawn.

4. The device of claim 3 wherein said retaining means comprises a projection projecting from said inner wall.

5. The device of claim 4 wherein said projection projects generally toward said exit end 6. The device of claim 5 wherein said projection is a hook.

7. The device of claim 1 wherein said second section is of a plastic material and comprises a succession of overlapping corrugations.

8. The device of claim 7 wherein said second section is capable of maintaining itself in any selected degree of extension and compression.

9. The device of claim 7 wherein said corrugations are asymmetrical, whereby they nest in one another when collapsed, said asymmetry also providing a toggle effect for maintaining the degree of extension and compression selected and providing a detectable stop upon collapse and upon extension of each corrugation.

10. A unitary tampon applicator, said applicator comprising:

a substantially rigid first tubular section for containing a tampon to be inserted into the vaginal canal, having an exit end through which said tampon is inserted into said canal;

a second tubular section abutting said first tubular section, said second section being collapsible and extensible; and a pusher member mounted at a first end thereof to an inner wall of said applicator at an end remote from said exit end and extending through said second section into said first section, a second end of said pusher member being biased away from said inner wall, said pusher member having a length such that when said second section is collapsed, said second end reaches at least to said exit end, and when said second section is extended, said second end reaches at most to a point at which said first and second tubular sections abut one another; wherein:

when said tampon is in said applicator prior to insertion into said canal, said second section is collapsed and said pusher member lies in a first position relative to said inner wall, between said inner wall and said tampon, in said first section; and when said tampon is to be inserted, said second section is extended by grasping said first section and said remote end and moving them away from one another, whereby said pusher member is withdrawn from between said inner wall and said tampon and, as a result of said bias, said second end thereof assumes a second position further from said inner wall than said first position and adjacent said tampon, thereby arming said applicator; such that when said exit end of said armed applicator is inserted in said canal and said second section is collapsed by grasping said first section and said remote end and moving them toward one another, said pusher member pushes said tampon out of said exit end into said canal.

11. The applicator of claim 10 further comprising a substantially rigid third tubular section abutting said collapsible and extensible second section, said third section serving as a handle for grasping said remote end.

12. The applicator of claim 10 further comprising means for retaining said tampon in said first section while said pusher member is being withdrawn.

13. The applicator of claim 12 wherein said retaining means comprises a projection projecting from said inner wall.

14. The applicator of claim 13 wherein said projection projects generally toward said exit end.

15. The applicator of claim 14 wherein said projection is a hook.

16. The applicator of claim 10 wherein said second section is of a plastic material and comprises a succession of overlapping corrugations.

17. The applicator of claim 16 wherein said second section is capable of maintaining itself in any selected degree of extension and compression.

18. The applicator of claim 16 wherein said corrugations are asymmetrical, whereby they nest in one another when collapsed, said asymmetry also providing a toggle effect for maintaining the degree of extension and compression selected and providing a detectable stop upon collapse and upon extension of each corrugation.

* * * * *